US007805010B2

(12) United States Patent
Posse et al.

(10) Patent No.: US 7,805,010 B2
(45) Date of Patent: Sep. 28, 2010

(54) CROSS-ONTOLOGICAL ANALYTICS FOR ALIGNMENT OF DIFFERENT CLASSIFICATION SCHEMES

(76) Inventors: Christian Posse, 2110 NW. 94th St., Seattle, WA (US) 98117; Antonio P Sanfilippo, P.O. Box 999, Richland, WA (US) 99352; Banu Gopalan, 2444 Warrensville Center Rd., Cleveland, OH (US) 44118; Roderick M Riensche, P.O. Box 999, Richland, WA (US) 99352; Robert L Baddeley, P.O. Box 999, Richland, WA (US) 99352

(*) Notice: Subject to any disclaimer, the term of this patent is extended or adjusted under 35 U.S.C. 154(b) by 1099 days.

(21) Appl. No.: 11/493,503

(22) Filed: Jul. 25, 2006

(65) Prior Publication Data

US 2008/0025617 A1 Jan. 31, 2008

(51) Int. Cl.
*G06K 9/62* (2006.01)
(52) U.S. Cl. ............... 382/224; 382/133; 707/E17.099
(58) Field of Classification Search ............ 382/133, 382/224, 226; 707/E17.099
See application file for complete search history.

(56) References Cited

U.S. PATENT DOCUMENTS 6,260,008 B1 * 7/2001 Sanfilippo .............. 704/9
6,487,545 B1 * 11/2002 Wical .................. 706/45

2006/0242190 A1* 10/2006 Wnek .................. 707/102

OTHER PUBLICATIONS

Posse et al. "Cross-Ontological Analytics: Combining Associative and Hierarchical Relations in the Gene Ontologies to Assess Gene Product Similarity" computational Science- ICCS 2006, Part II, Second International Workshop on Bioinformatics Research and Applications (IWBRA06) LNCS 3992, pp. 871-878, May 12, 2006.*
Chabalier et al, "A transversal approach to compute semantic similarity between genes", In Proceedings of the Workshop on Biomedical Ontologies and Text Processing—European Conference on Computational Biology (ECCB'2005),pp. 3-8, Sep. 28, 2005.*

(Continued)

*Primary Examiner*—Bhavesh M Mehta
*Assistant Examiner*—Stephen R Koziol
(74) *Attorney, Agent, or Firm*—Allan C. Tuan

(57) ABSTRACT

Quantification of the similarity between nodes in multiple electronic classification schemes is provided by automatically identifying relationships and similarities between nodes within and across the electronic classification schemes. Quantifying the similarity between a first node in a first electronic classification scheme and a second node in a second electronic classification scheme involves finding a third node in the first electronic classification scheme, wherein a first product value of an inter-scheme similarity value between the second and third nodes and an intra-scheme similarity value between the first and third nodes is a maximum. A fourth node in the second electronic classification scheme can be found, wherein a second product value of an inter-scheme similarity value between the first and fourth nodes and an intra-scheme similarity value between the second and fourth nodes is a maximum. The maximum between the first and second product values represents a measure of similarity between the first and second nodes.

21 Claims, 6 Drawing Sheets

OTHER PUBLICATIONS

Sanfilippo, et al, Integrating Ontological Knowledge & Textual . . . Proceedings of BioNLP'06: Linking Natural Language Processing and Biology, New York, Jun. 8, 2006, (8 pgs).

Kalfoglou, et al., Ontology mapping: the state of the art, The Knowledge Engineering Review, vol. 18:1, 2003, pp. 1-31.

Posse, et al, Cross-Ontological Analytics:, Proc. of International Workshops on Bioinformatics Research & Applications, Reading, U.K., May 28-31, 2006, (8 pgs).

Jiang, et al.,Semantic Similarity Based on Corpus Statistics & Lexical Taxonomy, Proc of International Conf Research on Computational Linguistics (POCLING X), Taiwan,1997,1-15.

Resnik, Proceedings of the 14th International Joint Conf. on Artificial Intelligence, Montreal, 1995, pp. 448-453.

Lin, et al, Proceedings of the 15th International Conf. on Machine Learning, Madison, WI, 1998.

Delfs, et al, Proc. of German Bioinformatics Conference, Bielefeld, Germany, 2004, LNBI Springer.

Sanfilippo, et al, Aligning the Gene Ontologies, Standards and Ontologies for Functional Genomics, Philadelphia, PA, Oct. 23-26, 2004. (Presentation 14pgs).

Gopalan, et al, Small Business Technology Transfer Program, Phase I Final Progress Report, Ontological Annotation for Cross-Scale Discovery, NIGMS, NIH, (Jan./2006) pp. 1-20.

Sanfilippo, et al, Integrating Ontological Knowledge & Textual . . . Proceedings of BioNLP'06: Linking Natural Language Processing and Biology, New York, Jun. 8, 2006, (8 pgs).

Kalfoglou, et al., Ontology mapping: the state of the art, The Knowledge Engineering Review, vol. 18:1, 2003, pp. 1-31.

Posse, et al, Cross-Ontological Analytics:, Proc. of International Workshops on Bioinformatics Research & Applications, Reading, U.K., May 28-31, 2006, (8 pgs).

Jiang, et al.,Semantic Similarity Based on Corpus Statistics & Lexical Taxonomy, Proc of International Conf Research on Computational Linguistics (POCLING X), Taiwan,1997,1-15.

Resnik, Proceedings of the 14th International Joint Conf. on Artificial Intelligence, Montreal, 1995, pp. 448-453.

Lin, et al, Proceedings of the 15th International Conf. on Machine Learning, Madison, WI, 1998.

Delfs, et al, Proc. of German Bioinformatics Conference, Bielefeld, Germany, 2004, LNBI Springer.

Sanfilippo, et al, Aligning the Gene Ontologies, Standards and Ontologies for Functional Genomics, Philadelphia, PA, Oct. 23-26, 2004. (Presentation 14pgs).

Gopalan, et al, Small Business Technology Transfer Program, Phase I Final Progress Report, Ontological Annotation for Cross-Scale Discovery, NIGMS, NIH, (Jan./2006) pp. 1-20.

Bodenreider, et al., Proceedings of Pacific Symposium on Biocomputer, 2005, pp. 104-115.

* cited by examiner

CROSS-ONTOLOGICAL ANALYTICS FOR ALIGNMENT OF DIFFERENT CLASSIFICATION SCHEMES

STATEMENT REGARDING FEDERALLY SPONSORED RESEARCH OR DEVELOPMENT

This invention was made with Government support under Contract DE-AC0576RLO1830 awarded by the U.S. Department of Energy. The Government has certain rights in the invention.

BACKGROUND

Techniques for measuring the similarity between nodes within a single electronic classification scheme have been developed and a number are well-known in the art. However, attempting to measure the similarity between nodes across different electronic classification schemes, which often address different domains of knowledge and/or contain orthogonal networks of concepts, often produces results that are not easily and/or reasonably integrated. This can be due to the fact that the certain similarity measures are appropriate for some schemes, but not others, and that each similarity measure can express distinct senses of similarity (i.e., intra-scheme and inter-scheme) making results from such similarity measures incomparable. Therefore, a need exists for improved similarity measurement methods and apparatuses, especially across different electronic classification schemes.

DESCRIPTION OF DRAWINGS

Embodiments of the invention are described below with reference to the following accompanying drawings.

DETAILED DESCRIPTION

Figure 1A:
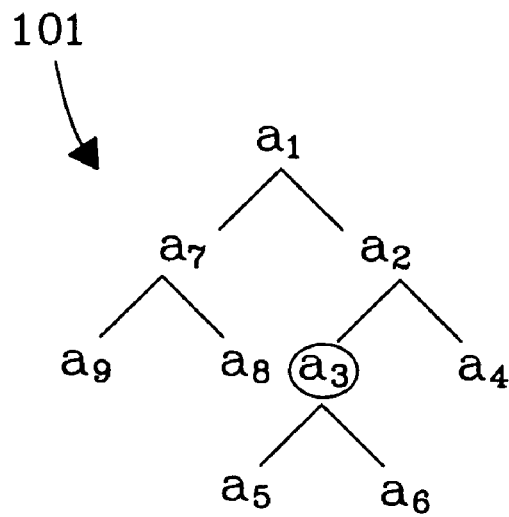
FIGS. 1a and 1b depict two embodiments of hierarchies as exemplary electronic classification schemes.

At least some aspects of the disclosure provide apparatuses and computer-implemented methods for quantifying the similarity between nodes in a plurality of electronic classification schemes. Exemplary quantification can provide automatic identification of relationships and similarity between nodes within (i.e., intra-scheme) and across (i.e., inter-scheme) electronic classification schemes. It can also enable searching of various data repositories. In some implementations, quantification of similarity can provide a data mining resource for revealing information. Accordingly, embodiments of the present invention can be implemented for a range of applications including, but not limited to bioinformatics, cross-scale scientific discovery, enterprise information integration, database schema alignment, and taxonomy alignment. The combined use of inter-scheme and intra-scheme measures to align distinct classification schemes and/or quantify the similarity between nodes of different schemes, according to embodiments of the present invention, is referred to herein as cross-ontological analytics (XOA).

An electronic classification scheme can refer to a plurality of nodes organized in a hierarchy. Exemplary classification schemes can include, but are not limited to, ontologies, taxonomies, category trees, lexicons, and directed acyclic graphs. Each node can represent a concept, and can be associated with one or more data items. A data item can refer to an electronic item comprising information that pertains, at least in part, to the domain of the electronic classification scheme with which it is associated. Exemplary information can include, but is not limited to, text, video segments, audio segments, images, graphs, database records, sensor data, annotations, and combinations thereof. An example of a data item can include, but is not limited to, a document containing text and/or images.

In some embodiments, for example, a node comprises a concept and is characterized by one or more features, wherein each feature is associated with one or more data items. "Features" as used in this context can refer to classification parameters that are relevant in providing a unique characterization of the node under analysis. In a specific example, a node can represent the concept of taste. Features of the taste concept can include genes and gene products that can be instrumental in distinguishing taste from other concepts, such as the sweet taste receptor gene (T1r3) and the protein gustducin found only in the taste buds. Features can occur as annotations of concepts in a database or data collection, or as data items found in association with concepts in a given context, e.g. a text such as an academic journal article, a scientific experiment, an audio-visual report.

In one embodiment of the present invention, quantification of the similarity between a first node in a first electronic classification scheme and a second node in a second electronic classification scheme comprises finding a third node among those in the first electronic classification scheme, wherein a first product value of an inter-scheme similarity value between the second and third nodes and an intra-scheme similarity value between the first and third nodes is a maximum. It further comprises finding a fourth node among those in the second electronic classification scheme, wherein a second product value of an inter-scheme similarity value between the first and fourth nodes and an intra-scheme similarity value between the second and fourth nodes is a maximum. The maximum between the first and second product values represents a measure of similarity between the first and second nodes.

In another embodiment, distinct electronic classifications schemes addressing different domains can be aligned by translating each associative relation across different electronic classification schemes into a hierarchical relation within a single electronic classification scheme.

Figure 1B:
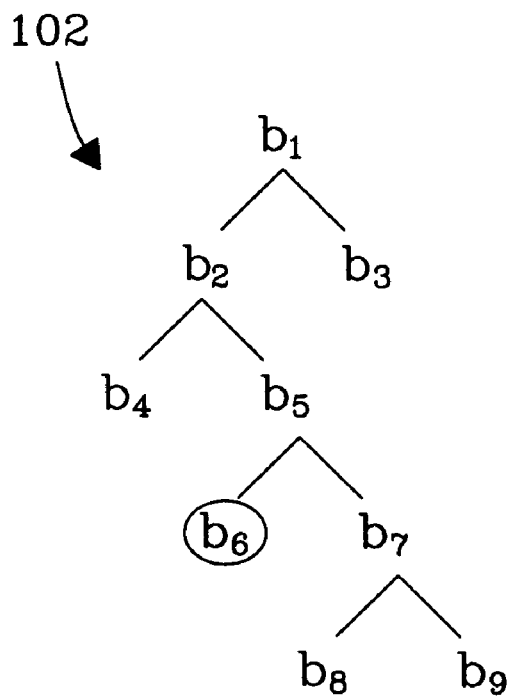

Referring to FIGS. 1a and 1b, two distinct hierarchies 101, 102 depict exemplary electronic classification schemes. The classification schemes can, for example, comprise ontologies addressing different knowledge domains, A and B, respectively. Each of the ontologies can comprise a plurality of nodes (e.g., $a_i$ and $b_i$), which can represent interrelated concepts, wherein the edges represent the relationships between concepts. According to embodiments of the present invention, aligning ontologies A and B and/or comparing the similarity between nodes across the two ontologies encompasses measures of both inter-scheme similarity values (i.e., intersim) and intra-scheme similarity values (i.e., intrasim). More specifically, for two nodes in different ontologies (e.g., $a_3$ and $b_6$), the XOA similarity can be defined as follows:

$$XOA(a_3, b_6) = \max \begin{cases} \max[\text{intrasim}(a_3, a_S) \cdot \text{intersim}(b_6, a_S)], \\ \max[\text{intrasim}(b_6, b_S) \cdot \text{intersim}(a_3, b_S)] \end{cases} \quad \text{Eqn. 1}$$

wherein $a_s$ and $b_s$ each represents the node in their respective ontologies that maximizes the intrasim-intersim product value. The maximum of the two product values can then be taken to represent the XOA similarity. In one sense, $a_s$ can be seen as a surrogate for $b_6$ in the same ontology as $a_3$. Similarly, $b_s$ can be seen as a surrogate for $a_3$ in the same ontology as $b_6$.

Exemplary measures for determining intra-scheme similarity values can include, but are not limited to information theoretic approaches, measures based on path length, and measures based on feature similarity across nodes. According to one embodiment of the present invention, a specific information theoretic approach comprises determining a least common superordinate (LCS) of intra-scheme node pairs and then determining an information content value for the least common superordinates, wherein the intra-scheme similarity values comprise the information content values. For example, referring to FIGS. 1a and 1b, if $a_s$ and $b_s$ are $a_4$ and $b_8$, respectively, then $a_3$ and $a_4$ would compose an intra-scheme node pair as would $b_6$ and $b_8$. The LCS of the two intra-scheme node pairs would be $a_2$ and $b_5$, respectively.

Details regarding one technique to determine the information content of the LCS are given by Resnik et al. (*Proceedings of the 14th International Joint Conference on Artificial Intelligence*, Montreal, 1995, pg. 448-453), which details are incorporated herein by reference. Briefly, Resnik et al. show that the semantic similarity between two concept nodes, c1 and c2, can be determined according to equation 2.

$$sim(c1,c2) = -\log p(lcs(c1,c2)) \qquad \text{Eqn. 2}$$

where p(n) is the probability of encountering n in a specific corpus. Therefore, referring to Eqn. 1 and to the ontologies shown in FIGS. 1a and 1b, the intra-scheme similarities between $a_3$ and $a_4$ and between $b_6$ and $b_8$ can be determined according to equations 3 and 4, respectively.

$$sim(c1,c2) = -\log p(lcs(c1,c2)) \qquad \text{Eqn. 2}$$

where p(n) is the probability of encountering n in a specific corpus. Therefore, referring to Eqn. 1 and to the ontologies shown in FIGS. 1a and 1b, the intra-scheme similarities between $a_3$ and $a_4$ and between $b_6$ and $b_8$ can be determined according to equations 3 and 4, respectively.

$$intrasim(a_3,a_4) = -\log p(a_2) \qquad \text{Eqn. 3}$$

$$intrasim(b_6,b_8) = -\log p(b_5) \qquad \text{Eqn. 4}$$

In many instances, a node and its LCS will be separated by one or more nodes. Accordingly, in some embodiments, determining the intra-scheme similarity value can further comprise accounting for the distance of each node from its respective LCS. For example, Jiang and Conrath (*Proceedings of the International Conference on Research in Computational Linguistics*, Taiwan, 1997) describe details, which are incorporated herein by reference, regarding a refinement to equation 2 that factors in the distance from each concept node to the LCS. The refinement to equation 2 is shown in equation 5.

$$sim(c1, c2) = \frac{1}{[2 \cdot \log p(LCS(c1, c2))] - [\log p(c1) + \log p(c2)]} \qquad \text{Eqn. 5}$$

Details regarding yet another modification are described by Lin (*Proceedings of the 15th International Conference on Machine Learning*, Madison, Wis., 1998), and are incorporated herein by reference. Lin's modification is shown in equation 6.

$$sim(c1, c2) = \frac{2 \cdot \log p(LCS(c1, c2))}{[\log p(c1) + \log p(c2)]} \qquad \text{Eqn. 6}$$

The examples described herein of techniques for determining the intra-scheme similarity values are for illustration and other techniques are both possible and encompassed by the scope of the present invention.

Exemplary measures for determining inter-scheme similarity values can include, but are not limited to, statistical techniques, logic-based techniques, and manual alignment techniques. According to one embodiment of the present invention, a specific statistical technique comprises representing each node as a vector signature and performing cosine measures between inter-scheme node pairs, wherein the inter-scheme similarity values comprise the results of the cosine measures. For example, referring to FIGS. 1a and 1b, inter-scheme similarity values can be determined by performing cosine measures between vector signatures of $a_3$ and $b_8$ and between vector signatures of $b_6$ and $a_4$. Additional details related to the instant embodiment have been described using a vector space model by Bodenreider et al. (*Proceedings of Pacific Symposium on Biocomputing*, 2005, pg. 104-115), which details are incorporated herein by reference.

Vector signatures, as used herein, can comprise data items including, but not limited to, textual evidence, visual evidence, audio evidence, and combinations thereof. In one embodiment, for example, a vector signature can be a vector of keywords from a document. In another embodiment, as described elsewhere herein, vector signatures can comprise gene ontology terms. Vectors can be normalized to compensate for the number of features and/or data items associated with particular concepts.

Figure 2:
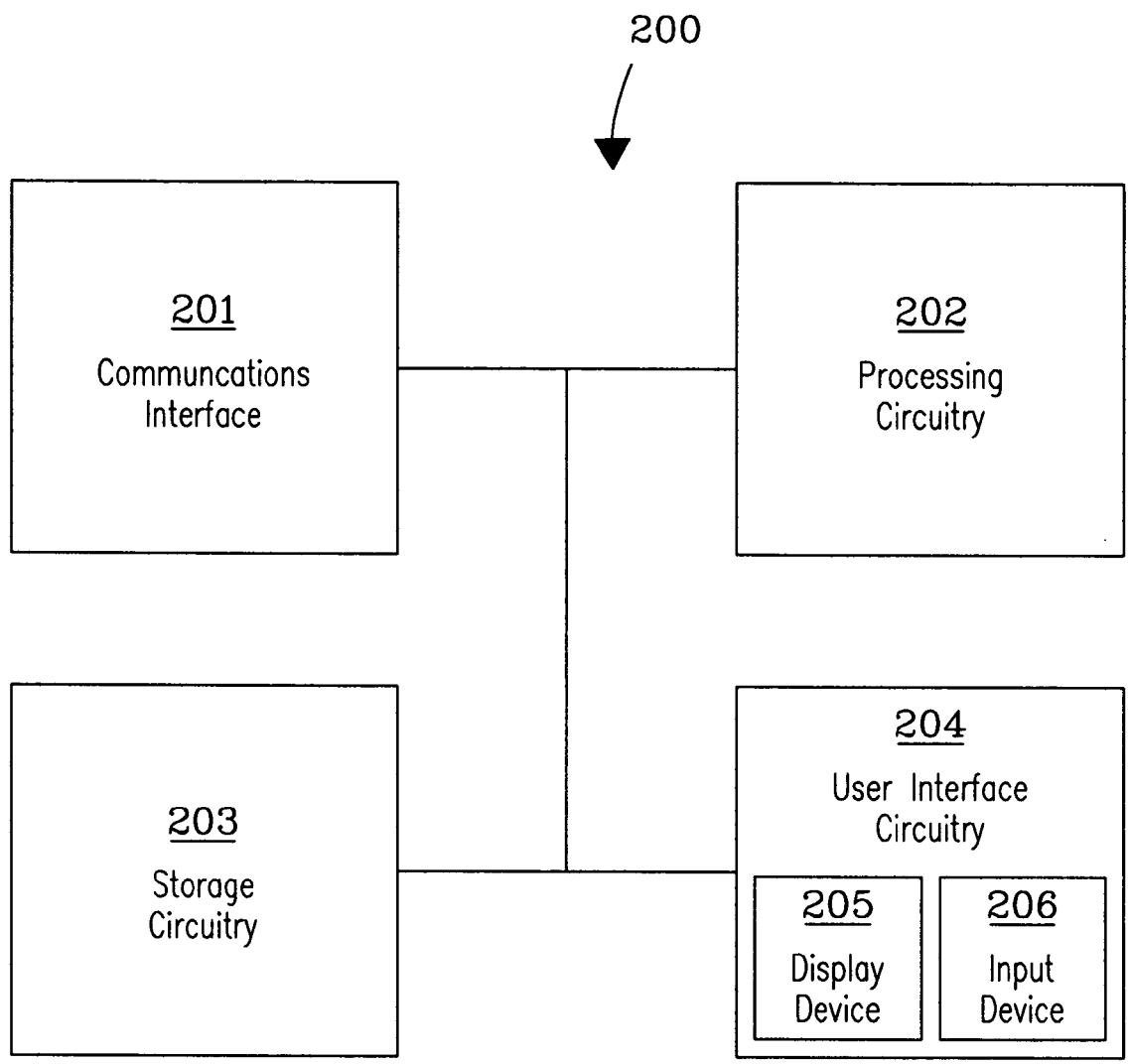
FIG. 2 is a block diagram depicting an embodiment of an apparatus for quantifying the similarity within and across different electronic classification schemes.

Referring to FIG. 2, an exemplary apparatus 200 for quantifying the similarity within and across different electronic classification schemes is illustrated. In the depicted embodiment, the apparatus is implemented as a computing device such as a work station, server, a handheld computing device, or a personal computer, and can include a communications interface 201, processing circuitry 202, storage circuitry 203, and, in some instances, a user interface, 204. Other embodiments of apparatus 200 can include more, less, and/or alternative components.

The communications interface 201 is arranged to implement communications of apparatus 200 with respect to a network, the internet, an external device, a remote data store, etc. Communication interface 201 can be implemented as a network interface card, serial connection, parallel connection, USB port, SCSI host bus adapter, Firewire interface, flash memory interface, floppy disk drive, wireless networking interface, PC card interface, PCI interface, IDE interface, SATA interface, or any other suitable arrangement for communicating with respect to apparatus 200. Accordingly, communications interface 201 can be arranged, for example, to communicate information bi-directionally with respect to apparatus 200.

In an exemplary embodiment, communications interface 201 can interconnect apparatus 200 to one or more persistent data stores having information including, but not limited to, electronic classification schemes, input data, and annotation data stored thereon. The data store can be locally attached to apparatus 200 or it can be remotely attached via a wireless and/or wired connection through communications interface 201. For example, the communications interface 201 can facilitate access and retrieval of information from one or more data stores containing structured and/or unstructured data that can be used to populate an electronic classification scheme with evidence and/or annotate the concepts contained therein.

In another embodiment, processing circuitry 202 is arranged to execute computer-readable instructions, process data, control data access and storage, issue commands, perform calculations, and control other desired operations. Processing circuitry 202 can operate to quantify the similarity between two nodes in different electronic classification schemes by finding a third node among those in the first electronic classification scheme, wherein a first product value of an inter-scheme similarity value between the second and third nodes and an intra-scheme similarity value between the first and third nodes is a maximum. It can further find a fourth node among those in the second electronic classification scheme, wherein a second product value of an inter-scheme similarity value between the first and fourth nodes and an intra-scheme similarity value between the second and fourth nodes is a maximum. The processing circuitry 202 can be configured to then determine the maximum between the first and second product values, which maximum represents a measure of similarity between the first and second nodes.

Furthermore, the processing circuitry 202 can operate to translate associative relations across nodes in first and second classification schemes into hierarchical relation within a single third electronic classification scheme.

Processing circuitry can comprise circuitry configured to implement desired programming provided by appropriate media in at least one embodiment. For example, the processing circuitry 202 can be implemented as one or more of a processor, and/or other structure, configured to execute computer-executable instructions including, but not limited to software, middleware, and/or firmware instructions, and/or hardware circuitry. Exemplary embodiments of processing circuitry 202 can include hardware logic, PGA, FPGA, ASIC, state machines, an/or other structures alone or in combination with a processor. The examples of processing circuitry described herein are for illustration and other configurations are both possible and appropriate.

Storage circuitry 203 can be configured to store programming such as executable code or instructions (e.g., software, middleware, and/or firmware), electronic data (e.g., electronic files, databases, data items, etc.), and/or other digital information and can include, but is not limited to, processor-usable media. Exemplary programming can include, but is not limited to programming configured to cause apparatus 200 to quantify the similarity between two nodes of different electronic classifications schemes. Processor-usable media can include, but is not limited to, any computer program product, data store, or article of manufacture that can contain, store, or maintain programming, data, and/or digital information for use by, or in connection with, an instruction execution system including the processing circuitry 202 in the exemplary embodiments described herein. Generally, exemplary processor-usable media can refer to electronic, magnetic, optical, electromagnetic, infrared, or semiconductor media. More specifically, examples of processor-usable media can include, but are not limited to floppy diskettes, zip disks, hard drives, random access memory, compact discs, and digital versatile discs.

At least some embodiments or aspects described herein can be implemented using programming configured to control appropriate processing circuitry and stored within appropriate storage circuitry and/or communicated via a network or via other transmission media. For example, programming can be provided via appropriate media, which can include articles of manufacture, and/or embodied within a data signal (e.g., modulated carrier waves, data packets, digital representations, etc.) communicated via an appropriate transmission medium. Such a transmission medium can include a communication network (e.g., the internet and/or a private network), wired electrical connection, optical connection, and/or electromagnetic energy, for example, via a communications interface, or provided using other appropriate communication structures or media. Exemplary programming, including processor-usable code, can be communicated as a data signal embodied in a carrier wave, in but one example.

User interface 204 can be configured to interact with a user and/or administrator, including conveying information to the user (e.g., displaying data for observation by the user, audibly communicating data to the user, etc.) and/or receiving inputs from the user (e.g., tactile inputs, voice instructions, etc.). Accordingly, in one exemplary embodiment, the user interface 204 can include a display device 205 configured to depict visual information, and a keyboard, mouse and/or other input device 206. Examples of a display device include cathode ray tubes and LCDs.

The embodiment shown in FIG. 2 can be an integrated unit configured to quantify the similarity between two nodes within and across different electronic classification schemes. Other configurations are possible, wherein apparatus 200 is configured as a networked server and one or more clients are configured to access the processing circuitry and/or storage circuitry for accessing electronic classification schemes, retrieving information, determining surrogate nodes and/or calculating similarity values.

Example

Implementing XOA in Bioinformatics and Gene Ontology Databases

Aspects of the present invention have been applied to combine associative and hierarchical relations in the gene ontologies to assess gene product similarity. Gene and gene product similarity can be a fundamental diagnostic measure in analyzing biological data and constructing predictive models for functional genomics. More specifically, the similarity between genes and/or gene products can be obtained by comparing gene ontology (GO) annotations associated with the genes and/or gene products. Accordingly, XOA can both validate results of currently-available search tools and serve as a stand-alone prediction tool. According to the instant example, GO terms can be used to identify relevant correlations between metagenome sequences and microorganisms by computing the similarity between GO terms associated with the metagenome sequences and the GO terms associated with the microorganisms.

The gene ontologies referred to herein provide three orthogonal networks of functional genomic concepts structured in terms of semantic relationships that include, but are not limited to inheritance and meronymy. In the present example, the three networks encode biological process (BP), molecular function (MF), and cellular component (CC) properties of genes and gene products.

Figure 3:
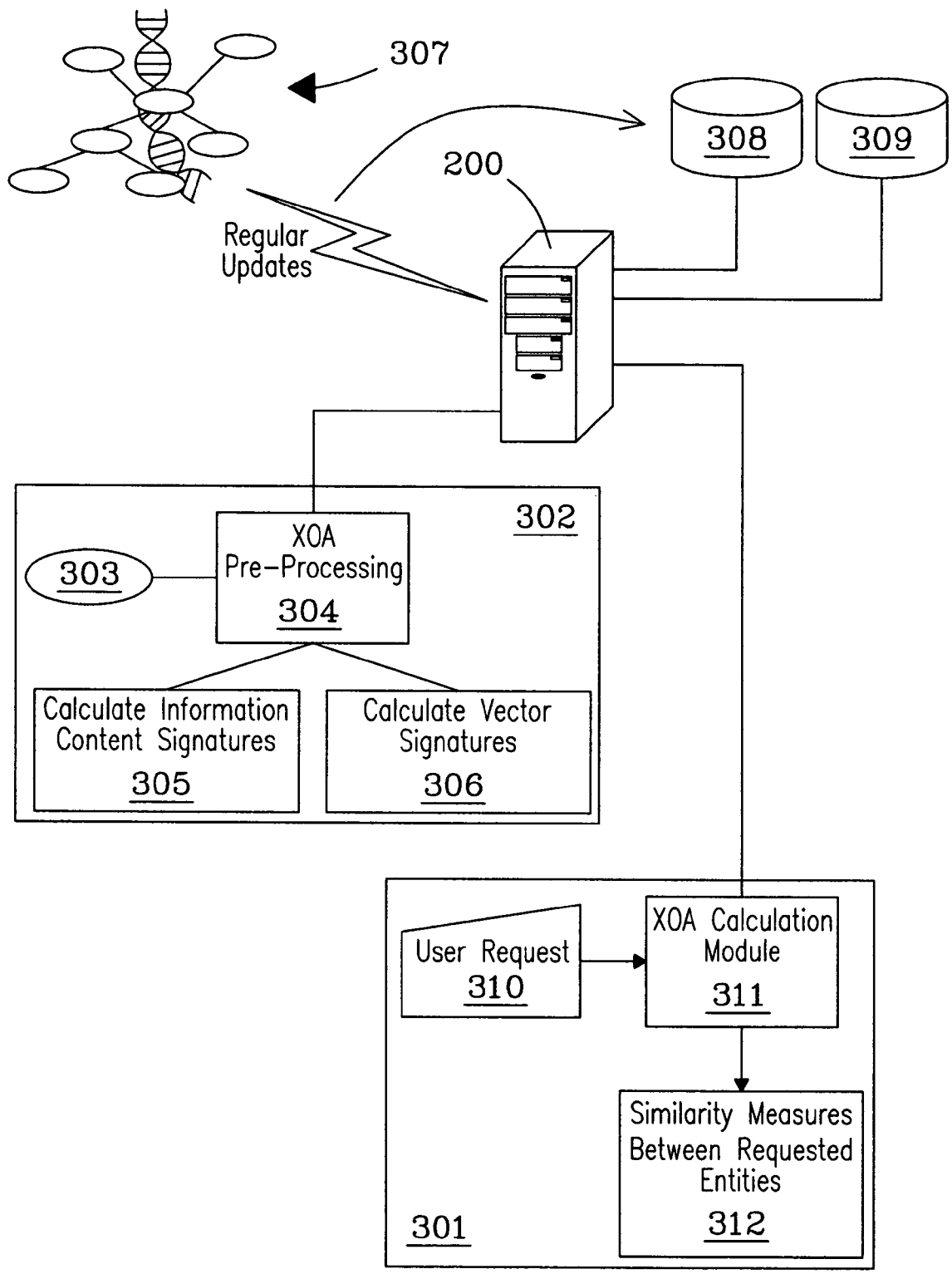
FIG. 3 is an illustration of a system architecture according to one embodiment.

Referring to FIG. 3, an embodiment of a system architecture is illustrated. The XOA apparatus 200 can receive regular data updates (e.g., GO terms for microorganisms and metagenome sequences of interest) from gene ontology sources 307 via a communications interface. The data from the gene ontologies can be stored on storage circuitry such as data storage device 308, 309 in, for example, GO database tables. In some instances, a selected dataset 303 (e.g., microorganisms and metagenome sequences of interest) can be arranged 302 prior to XOA calculations 301.

Pre-processing 304 can include, but is not limited to, creating a set of features for each GO term, where the features can be annotations of GO terms in a database, or data items found in association with concepts in a given context, as explained elsewhere herein. The sets of features are then used to compute the information content 305 and vector signatures 306 for each GO term It can further comprise calculating information contents and vector signatures for some or all applicable node-pair combinations depending on the desired analysis. For example, information contents and vector signatures can be calculated individually for each request and/or node pair comparison as the request is received. Alternatively, the information contents and vector signatures can be calculated for all possible node pairs independently of a particular request and then stored in a data storage device 309.

With reference to the bio-informatics domain, XOA measurements can be used to assess similarity across genes, proteins, microorganisms and any other biological entity that can be characterized by GO terms. The protein comparison shown in Table 1 provides an exemplification of this functionality. First each protein is associated with its related GO terms. Then all possible measurements are made across the GO terms sets for the two proteins. The emerging similarity values are reduced to a single value which represents the similarity score for the two proteins. Such a reduction can be performed as follows. Let P1 and P2 be two proteins. Let c11, c12, ..., c1n denote the set of GO codes associated with P1 and c21, c22, ..., c2m the set of GO codes associated with P2. The XOA similarity between P1 and P2 is defined as in Eqn. 7, where i=1, ..., n and j=1, ..., m.

$$XOA(GP1, GP2) = \max\{XOA(c1i, c2j)\} \qquad \text{Eqn. 7}$$

Other methods, such as a selecting the mode or the mean value, can also used.

TABLE 1

An exemplary representation of how protein similarity is performed through XOA. P-values indicate the significance of each score by quantifying the probability that a score higher than the one observed might occur.

| Proteins under comparison and relative GO terms | | Intra- and Inter-scheme similarity algorithms used | | | | | |
|---|---|---|---|---|---|---|---|
| | | Jiang & Conrath | | Lin | | Resnik | |
| | | XOA Score | p-value | XOA Score | p-value | XOA Score | p-value |
| EGF_HUMAN | EREG_HUMAN | 33.958 | 0 | 1 | 0 | 12.983 | 0 |
| GO:0005155 (MF) | GO:0005154 (MF) | 32.064 | 0 | 0.932 | 0 | 12.983 | 0 |
| GO:0005155 (MF) | GO:0008083 (MF) | 25.258 | 0.013 | 0.64 | 0.015 | 7.726 | 0.019 |
| GO:0005155 (MF) | GO:0000074 (BP) | 6.074 | 0.577 | 0.131 | 0.434 | 1.554 | 0.554 |
| GO:0005155 (MF) | GO:0001525 (BP) | 10.898 | 0.323 | 0.284 | 0.181 | 3.909 | 0.17 |
| GO:0005155 (MF) | GO:0007173 (BP) | 12.747 | 0.246 | 0.371 | 0.116 | 5.161 | 0.099 |
| GO:0005155 (MF) | GO:0007267 (BP) | 6.072 | 0.577 | 0.134 | 0.428 | 1.468 | 0.567 |
| GO:0005155 (MF) | GO:0008283 (BP) | 7.425 | 0.496 | 0.188 | 0.283 | 2.271 | 0.316 |
| GO:0005155 (MF) | GO:0030154 (BP) | 12.191 | 0.269 | 0.306 | 0.163 | 3.63 | 0.191 |
| GO:0005155 (MF) | GO:0005615 (CC) | 10.314 | 0.349 | 0.262 | 0.201 | 3.123 | 0.219 |
| GO:0005155 (MF) | GO:0005887 (CC) | 4.78 | 0.658 | 0.073 | 0.64 | 0.761 | 0.706 |
| GO:0005509 (MF) | GO:0005154 (MF) | 23.527 | 0.025 | 0.603 | 0.021 | 6.594 | 0.042 |
| GO:0005509 (MF) | GO:0008083 (MF) | 26.692 | 0.007 | 0.727 | 0.007 | 6.594 | 0.042 |
| GO:0005509 (MF) | GO:0000074 (BP) | 27.042 | 0.006 | 0.648 | 0.014 | 4.816 | 0.117 |
| GO:0005509 (MF) | GO:0001525 (BP) | 20.737 | 0.053 | 0.374 | 0.113 | 4.706 | 0.122 |
| GO:0005509 (MF) | GO:0007173 (BP) | 21.996 | 0.039 | 0.503 | 0.049 | 5.207 | 0.096 |
| GO:0005509 (MF) | GO:0007267 (BP) | 28.544 | 0.003 | 0.785 | 0.003 | 8.408 | 0.011 |
| GO:0005509 (MF) | GO:0008283 (BP) | 23.564 | 0.024 | 0.247 | 0.213 | 1.902 | 0.437 |
| GO:0005509 (MF) | GO:0030154 (BP) | 24.371 | 0.018 | 0.622 | 0.018 | 6.628 | 0.041 |
| GO:0005509 (MF) | GO:0005615 (CC) | 30.5 | 0.001 | 0.837 | 0.002 | 6.402 | 0.046 |
| GO:0005509 (MF) | GO:0005887 (CC) | 27.136 | 0.006 | 0.711 | 0.008 | 6.592 | 0.042 |
| GO:0005515 (MF) | GO:0005154 (MF) | 26.959 | 0.006 | 0.631 | 0.017 | 6.176 | 0.053 |
| GO:0005515 (MF) | GO:0008083 (MF) | 30.667 | 0.001 | 0.784 | 0.003 | 6.176 | 0.053 |
| GO:0005515 (MF) | GO:0000074 (BP) | 25.436 | 0.012 | 0.609 | 0.02 | 4.447 | 0.134 |
| GO:0005515 (MF) | GO:0001525 (BP) | 19.377 | 0.074 | 0.349 | 0.131 | 4.39 | 0.138 |
| GO:0005515 (MF) | GO:0007173 (BP) | 20.51 | 0.057 | 0.469 | 0.062 | 4.767 | 0.119 |
| GO:0005515 (MF) | GO:0007267 (BP) | 26.132 | 0.009 | 0.718 | 0.007 | 7.698 | 0.019 |
| GO:0005515 (MF) | GO:0008283 (BP) | 22.019 | 0.039 | 0.23 | 0.23 | 1.909 | 0.437 |
| GO:0005515 (MF) | GO:0030154 (BP) | 22.758 | 0.031 | 0.58 | 0.026 | 6.184 | 0.053 |
| GO:0005515 (MF) | GO:0005615 (CC) | 27.949 | 0.004 | 0.767 | 0.004 | 5.866 | 0.064 |
| GO:0005515 (MF) | GO:0005887 (CC) | 25.487 | 0.012 | 0.667 | 0.012 | 6.192 | 0.052 |
| GO:0008083 (MF) | GO:0005154 (MF) | 27.152 | 0.006 | 0.694 | 0.01 | 7.726 | 0.019 |
| GO:0008083 (MF) | GO:0008083 (MF) | 33.958 | 0 | 1 | 0 | 9.275 | 0.005 |
| GO:0008083 (MF) | GO:0000074 (BP) | 6.829 | 0.529 | 0.201 | 0.264 | 1.865 | 0.442 |
| GO:0008083 (MF) | GO:0001525 (BP) | 8.596 | 0.433 | 0.218 | 0.242 | 2.579 | 0.292 |
| GO:0008083 (MF) | GO:0007173 (BP) | 10.794 | 0.328 | 0.276 | 0.189 | 3.071 | 0.224 |
| GO:0008083 (MF) | GO:0007267 (BP) | 5.677 | 0.6 | 0.149 | 0.369 | 1.385 | 0.577 |
| GO:0008083 (MF) | GO:0008283 (BP) | 9.983 | 0.366 | 0.294 | 0.174 | 2.727 | 0.244 |
| GO:0008083 (MF) | GO:0030154 (BP) | 6.104 | 0.575 | 0.103 | 0.567 | 0.996 | 0.651 |
| GO:0008083 (MF) | GO:0005615 (CC) | 12.579 | 0.253 | 0.342 | 0.136 | 3.123 | 0.219 |

TABLE 1-continued

An exemplary representation of how protein similarity is performed through XOA. P-values indicate the significance of each score by quantifying the probability that a score higher than the one observed might occur.

| Proteins under comparison and relative GO terms | | Intra- and Inter-scheme similarity algorithms used | | | | | |
|---|---|---|---|---|---|---|---|
| | | Jiang & Conrath | | Lin | | Resnik | |
| | | XOA Score | p-value | XOA Score | p-value | XOA Score | p-value |
| GO:0008083 (MF) | GO:0005887 (CC) | 6.978 | 0.522 | 0.105 | 0.564 | 0.97 | 0.654 |
| GO:0000187 (BP) | GO:0005154 (MF) | 8.406 | 0.443 | 0.189 | 0.281 | 2.316 | 0.313 |
| GO:0000187 (BP) | GO:0008083 (MF) | 4.684 | 0.665 | 0.086 | 0.607 | 1.012 | 0.647 |
| GO:0000187 (BP) | GO:0000074 (BP) | 20.539 | 0.056 | 0.364 | 0.119 | 3.838 | 0.181 |
| GO:0000187 (BP) | GO:0001525 (BP) | 10.831 | 0.326 | 0.142 | 0.394 | 1.933 | 0.365 |
| GO:0000187 (BP) | GO:0007173 (BP) | 21.145 | 0.048 | 0.476 | 0.06 | 5.826 | 0.065 |
| GO:0000187 (BP) | GO:0007267 (BP) | 23.735 | 0.023 | 0.521 | 0.043 | 5.567 | 0.075 |
| GO:0000187 (BP) | GO:0008283 (BP) | 15.933 | 0.147 | 0.16 | 0.34 | 1.719 | 0.53 |
| GO:0000187 (BP) | GO:0030154 (BP) | 17.489 | 0.11 | 0.173 | 0.315 | 1.958 | 0.362 |
| GO:0000187 (BP) | GO:0005615 (CC) | 3.845 | 0.718 | 0.084 | 0.61 | 0.902 | 0.67 |
| GO:0000187 (BP) | GO:0005887 (CC) | 5.296 | 0.625 | 0.095 | 0.585 | 0.94 | 0.662 |
| GO:0006260 (BP) | GO:0005154 (MF) | 22.73 | 0.031 | 0.583 | 0.026 | 6.371 | 0.047 |
| GO:0006260 (BP) | GO:0008083 (MF) | 25.788 | 0.01 | 0.703 | 0.009 | 6.371 | 0.047 |
| GO:0006260 (BP) | GO:0000074 (BP) | 26.08 | 0.009 | 0.625 | 0.018 | 4.539 | 0.13 |
| GO:0006260 (BP) | GO:0001525 (BP) | 19.919 | 0.065 | 0.359 | 0.125 | 4.52 | 0.131 |
| GO:0006260 (BP) | GO:0007173 (BP) | 21.109 | 0.049 | 0.483 | 0.057 | 4.837 | 0.116 |
| GO:0006260 (BP) | GO:0007267 (BP) | 26.517 | 0.008 | 0.729 | 0.007 | 7.811 | 0.018 |
| GO:0006260 (BP) | GO:0008283 (BP) | 22.635 | 0.032 | 0.235 | 0.224 | 1.842 | 0.444 |
| GO:0006260 (BP) | GO:0030154 (BP) | 23.725 | 0.023 | 0.597 | 0.023 | 6.367 | 0.047 |
| GO:0006260 (BP) | GO:0005615 (CC) | 28.444 | 0.003 | 0.78 | 0.004 | 5.97 | 0.061 |
| GO:0006260 (BP) | GO:0005887 (CC) | 26.373 | 0.008 | 0.691 | 0.01 | 6.407 | 0.046 |
| GO:0007001 (BP) | GO:0005154 (MF) | 16.587 | 0.131 | 0.425 | 0.083 | 4.649 | 0.125 |
| GO:0007001 (BP) | GO:0008083 (MF) | 18.819 | 0.084 | 0.513 | 0.046 | 4.649 | 0.125 |
| GO:0007001 (BP) | GO:0000074 (BP) | 20.984 | 0.05 | 0.456 | 0.069 | 3.297 | 0.207 |
| GO:0007001 (BP) | GO:0001525 (BP) | 15.391 | 0.161 | 0.262 | 0.201 | 3.295 | 0.207 |
| GO:0007001 (BP) | GO:0007173 (BP) | 17.49 | 0.11 | 0.352 | 0.129 | 3.502 | 0.197 |
| GO:0007001 (BP) | GO:0007267 (BP) | 20.597 | 0.055 | 0.528 | 0.041 | 5.656 | 0.071 |
| GO:0007001 (BP) | GO:0008283 (BP) | 20.617 | 0.055 | 0.211 | 0.249 | 1.781 | 0.499 |
| GO:0007001 (BP) | GO:0030154 (BP) | 22.049 | 0.038 | 0.435 | 0.078 | 4.641 | 0.125 |
| GO:0007001 (BP) | GO:0005615 (CC) | 20.649 | 0.054 | 0.566 | 0.029 | 4.334 | 0.14 |
| GO:0007001 (BP) | GO:0005887 (CC) | 19.72 | 0.068 | 0.505 | 0.049 | 4.682 | 0.124 |
| GO:0007173 (BP) | GO:0005154 (MF) | 13.5 | 0.219 | 0.398 | 0.099 | 5.161 | 0.099 |
| GO:0007173 (BP) | GO:0008083 (MF) | 10.794 | 0.328 | 0.276 | 0.189 | 3.071 | 0.224 |
| GO:0007173 (BP) | GO:0000074 (BP) | 16.572 | 0.131 | 0.322 | 0.152 | 3.797 | 0.183 |
| GO:0007173 (BP) | GO:0001525 (BP) | 12.65 | 0.251 | 0.327 | 0.148 | 4.29 | 0.141 |
| GO:0007173 (BP) | GO:0007173 (BP) | 33.958 | 0 | 1 | 0 | 12.097 | 0.001 |
| GO:0007173 (BP) | GO:0007267 (BP) | 24.006 | 0.021 | 0.528 | 0.04 | 5.567 | 0.075 |
| GO:0007173 (BP) | GO:0008283 (BP) | 16.204 | 0.14 | 0.162 | 0.337 | 1.719 | 0.53 |
| GO:0007173 (BP) | GO:0030154 (BP) | 17.76 | 0.105 | 0.356 | 0.126 | 4 | 0.159 |
| GO:0007173 (BP) | GO:0005615 (CC) | 3.889 | 0.717 | 0.086 | 0.61 | 0.902 | 0.67 |
| GO:0007173 (BP) | GO:0005887 (CC) | 5.395 | 0.619 | 0.075 | 0.637 | 0.832 | 0.688 |
| GO:0008284 (BP) | GO:0005154 (MF) | 7.513 | 0.49 | 0.198 | 0.268 | 2.596 | 0.291 |
| GO:0008284 (BP) | GO:0008083 (MF) | 9.404 | 0.394 | 0.265 | 0.196 | 2.674 | 0.287 |
| GO:0008284 (BP) | GO:0000074 (BP) | 24.483 | 0.017 | 0.521 | 0.043 | 5.157 | 0.099 |
| GO:0008284 (BP) | GO:0001525 (BP) | 12.137 | 0.27 | 0.173 | 0.315 | 2.391 | 0.308 |
| GO:0008284 (BP) | GO:0007173 (BP) | 14.236 | 0.194 | 0.157 | 0.349 | 2.064 | 0.335 |
| GO:0008284 (BP) | GO:0007267 (BP) | 17.343 | 0.114 | 0.171 | 0.317 | 1.719 | 0.53 |
| GO:0008284 (BP) | GO:0008283 (BP) | 31.99 | 0 | 0.902 | 0.001 | 9.095 | 0.006 |
| GO:0008264 (BP) | GO:0030154 (BP) | 18.795 | 0.084 | 0.185 | 0.29 | 1.719 | 0.53 |
| GO:0008284 (BP) | GO:0005615 (CC) | 3.608 | 0.734 | 0.106 | 0.555 | 1.175 | 0.617 |
| GO:0008284 (BP) | GO:0005887 (CC) | 5.819 | 0.591 | 0.06 | 0.683 | 0.652 | 0.75 |
| GO:0005576 (CC) | GO:0005154 (MF) | 24.612 | 0.016 | 0.631 | 0.017 | 6.898 | 0.035 |
| GO:0005576 (CC) | GO:0008083 (MF) | 27.924 | 0.004 | 0.761 | 0.005 | 6.898 | 0.035 |
| GO:0005576 (CC) | GO:0000074 (BP) | 27.623 | 0.005 | 0.662 | 0.013 | 4.919 | 0.111 |
| GO:0005576 (CC) | GO:0001525 (BP) | 21.174 | 0.048 | 0.382 | 0.107 | 4.814 | 0.117 |
| GO:0005576 (CC) | GO:0007173 (BP) | 22.461 | 0.034 | 0.514 | 0.046 | 5.316 | 0.092 |
| GO:0005576 (CC) | GO:0007267 (BP) | 29.145 | 0.002 | 0.801 | 0.003 | 8.585 | 0.009 |
| GO:0005576 (CC) | GO:0008283 (BP) | 24.061 | 0.02 | 0.252 | 0.209 | 1.933 | 0.365 |
| GO:0005576 (CC) | GO:0030154 (BP) | 24.933 | 0.015 | 0.636 | 0.016 | 6.78 | 0.038 |
| GO:0005576 (CC) | GO:0005615 (CC) | 32.159 | 0 | 0.882 | 0.001 | 6.75 | 0.039 |
| GO:0005576 (CC) | GO:0005887 (CC) | 27.722 | 0.004 | 0.726 | 0.007 | 6.734 | 0.039 |
| GO:0005634 (CC) | GO:0005154 (MF) | 20.398 | 0.058 | 0.523 | 0.042 | 5.717 | 0.07 |
| GO:0005634 (CC) | GO:0008083 (MF) | 23.143 | 0.028 | 0.63 | 0.017 | 5.717 | 0.07 |
| GO:0005634 (CC) | GO:0000074 (BP) | 25.195 | 0.013 | 0.604 | 0.021 | 4.354 | 0.139 |
| GO:0005634 (CC) | GO:0001525 (BP) | 17.849 | 0.103 | 0.322 | 0.152 | 4.049 | 0.158 |
| GO:0005634 (CC) | GO:0007173 (BP) | 18.921 | 0.082 | 0.433 | 0.08 | 4.314 | 0.141 |

TABLE 1-continued

An exemplary representation of how protein similarity is performed through XOA. P-values indicate the significance of each score by quantifying the probability that a score higher than the one observed might occur.

| Proteins under comparison and relative GO terms | | Intra- and Inter-scheme similarity algorithms used | | | | | |
|---|---|---|---|---|---|---|---|
| | | Jiang & Conrath | | Lin | | Resnik | |
| | | XOA Score | p-value | XOA Score | p-value | XOA Score | p-value |
| GO:0005634 (CC) | GO:0007267 (BP) | 23.651 | 0.023 | 0.65 | 0.014 | 6.967 | 0.032 |
| GO:0005634 (CC) | GO:0008283 (BP) | 20.282 | 0.06 | 0.212 | 0.249 | 1.822 | 0.446 |
| GO:0005634 (CC) | GO:0030154 (BP) | 20.973 | 0.05 | 0.535 | 0.038 | 5.703 | 0.071 |
| GO:0005634 (CC) | GO:0005615 (CC) | 25.446 | 0.012 | 0.698 | 0.009 | 5.341 | 0.091 |
| GO:0005634 (CC) | GO:0005887 (CC) | 24.766 | 0.015 | 0.62 | 0.019 | 5.748 | 0.068 |
| GO:0005886 (CC) | GO:0005154 (MF) | 3.873 | 0.717 | 0.103 | 0.567 | 0.926 | 0.666 |
| GO:0005886 (CC) | GO:0008083 (MF) | 4.853 | 0.653 | 0.112 | 0.537 | 0.97 | 0.654 |
| GO:0005886 (CC) | GO:0000074 (BP) | 4.167 | 0.697 | 0.105 | 0.564 | 0.908 | 0.67 |
| GO:0005886 (CC) | GO:0001525 (BP) | 2.01 | 0.85 | 0.042 | 0.774 | 0.505 | 0.795 |
| GO:0005886 (CC) | GO:0007173 (BP) | 3.232 | 0.759 | 0.088 | 0.599 | 1.123 | 0.626 |
| GO:0005886 (CC) | GO:0007267 (BP) | 5.853 | 0.59 | 0.155 | 0.355 | 1.4 | 0.577 |
| GO:0005886 (CC) | GO:0008283 (BP) | 2.622 | 0.803 | 0.069 | 0.652 | 0.627 | 0.756 |
| GO:0005886 (CC) | GO:0030154 (BP) | 2.018 | 0.85 | 0.044 | 0.754 | 0.455 | 0.812 |
| GO:0005886 (CC) | GO:0005615 (CC) | 22.389 | 0.034 | 0.269 | 0.193 | 2.131 | 0.329 |
| GO:0005886 (CC) | GO:0005887 (CC) | 32.739 | 0 | 0.923 | 0 | 7.283 | 0.026 |
| GO:0016021 (CC) | GO:0005154 (MF) | 16.726 | 0.128 | 0.429 | 0.082 | 4.688 | 0.123 |
| GO:0016021 (CC) | GO:0008083 (MF) | 18.977 | 0.081 | 0.517 | 0.044 | 4.688 | 0.123 |
| GO:0016021 (CC) | GO:0000074 (BP) | 19.186 | 0.078 | 0.46 | 0.066 | 3.331 | 0.206 |
| GO:0016021 (CC) | GO:0001525 (BP) | 14.687 | 0.181 | 0.264 | 0.199 | 3.323 | 0.206 |
| GO:0016021 (CC) | GO:0007173 (BP) | 16.288 | 0.138 | 0.36 | 0.123 | 3.543 | 0.195 |
| GO:0016021 (CC) | GO:0007267 (BP) | 19.426 | 0.073 | 0.534 | 0.038 | 5.722 | 0.07 |
| GO:0016021 (CC) | GO:0008283 (BP) | 18.672 | 0.086 | 0.208 | 0.254 | 1.395 | 0.577 |
| GO:0016021 (CC) | GO:0030154 (BP) | 19.763 | 0.068 | 0.439 | 0.076 | 4.681 | 0.124 |
| GO:0016021 (CC) | GO:0005615 (CC) | 24.996 | 0.014 | 0.573 | 0.028 | 4.384 | 0.138 |
| GO:0016021 (CC) | GO:0005887 (CC) | 30.132 | 0.001 | 0.71 | 0.008 | 4.715 | 0.122 |

Figure 4:
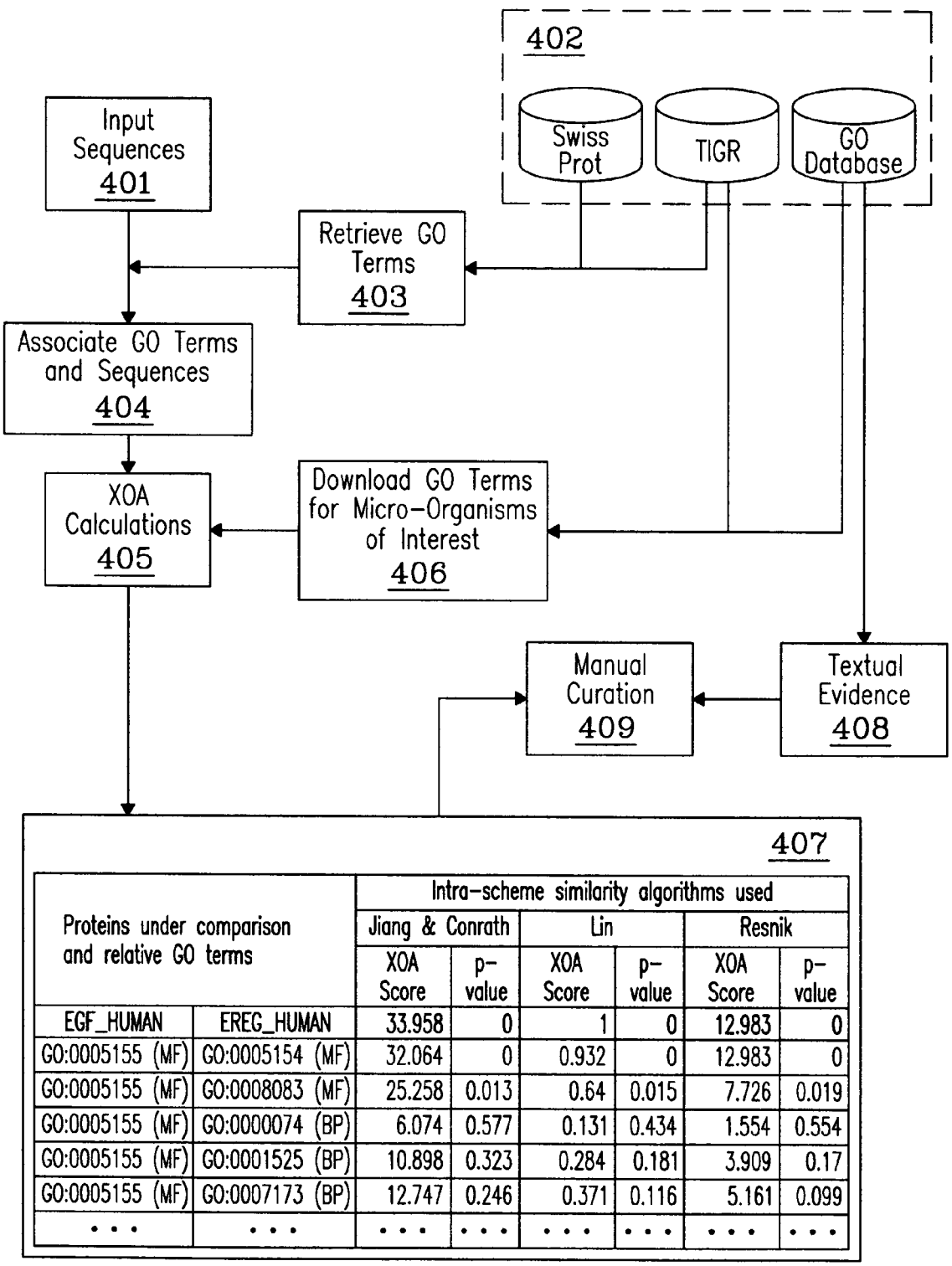
FIG. 4 is a flowchart depicting one embodiment of a method for XOA.

According to one embodiment, the similarity values across GO terms shown in the representation in Table 1 can be determined according to the method depicted in the flow chart of FIG. 4. One or more sequences 401, which can compose some or all of a selected dataset 303 (see FIG. 3), can be input for analysis. GO terms are retrieved 403 from data stores 402, which in the instant embodiment include the Swiss-Prot protein knowledgebase, the Institute for Genomic Research (TIGR) databases, and the Gene Ontology. The biological entities under comparison (e.g. proteins, genes, microorganism) are annotated with the appropriate GO terms 404, 406. The XOA similarity between GO terms associated with the sequences and GO terms associated with the biological entity of interest can be calculated 405 according to embodiments described elsewhere herein. According to the present example, a table 407 similar to Table 1 can be populated with the XOA similarity values and can, for instance, be stored in a data storage device or outputted to a display device. In some instances, the GO terms, sequences, microorganisms, and/or the XOA similarity data can be curated 409 with additional evidence such as textual descriptions of GO terms 408, thereby enhancing the analysis results.

One or more users can access the XOA apparatus, for example, through a web interface. For instance, according to the present example, referring to FIG. 3, the user's request 310 for analysis of certain sequences and/or microorganisms can cause interrogation of data stored in data storage devices (e.g., storage devices 308 and 309), which can contain GO database tables, information content values, and/or vector signatures. The XOA apparatus 200 can then process the user's request by determining the appropriate XOA similarities according embodiments of an XOA calculation module 311 described elsewhere herein. The similarity measures between requested entities 312 can then be outputted to the user via the web interface.

Figure 5:
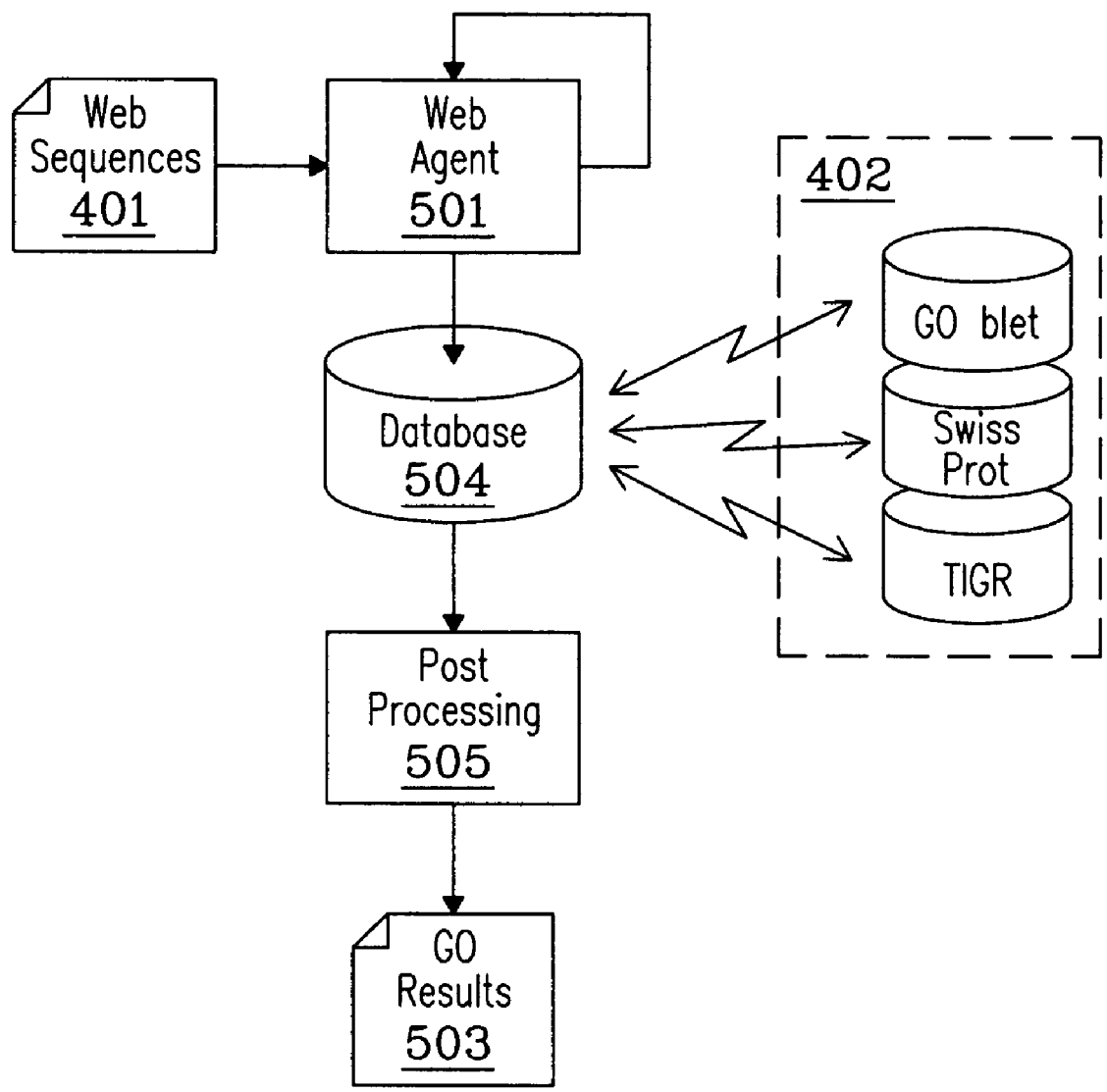
FIG. 5 is a flowchart depicting one embodiment of an XOA process having a web interface.

An exemplary implementation of the web interface, which is an example of the user interface 204 described elsewhere herein, is depicted in FIG. 5. A web agent 501 can process the input sequence 401 against one or more search services 402 and store intermediate results in a local database 504. The intermediate results can then be further processed by a post-processor 505 that, for example, performs extraction, parsing, and integration for creating the final results 503. For each input sequence, the web agent 501 can retrieve all relevant GO terms using software that performs annotation of anonymous sequences (e.g., the GOblet service). The agent can invoke independent GOblet sessions in intermittent intervals to avoid overloading the web service and allowing enough suspension time for returned results. The web agent 501 can store the GOblet-returned results in the local database 504. Exemplary results can include, but are not limited to, accession number, E-value, organism name, protein name, and GO terms. Typically, results from the search services produce disjunctive annotations. In other words, the retrieved results from different ontologies do not associate relationships between specific sequences.

In one embodiment, XOA similarities can be determined by following a vector space model approach. For instance, in the present example, the inter-scheme similarity values can be determined according to a vector space model and the intra-scheme similarity values can be determined according to an information content approach.

Figure 6:
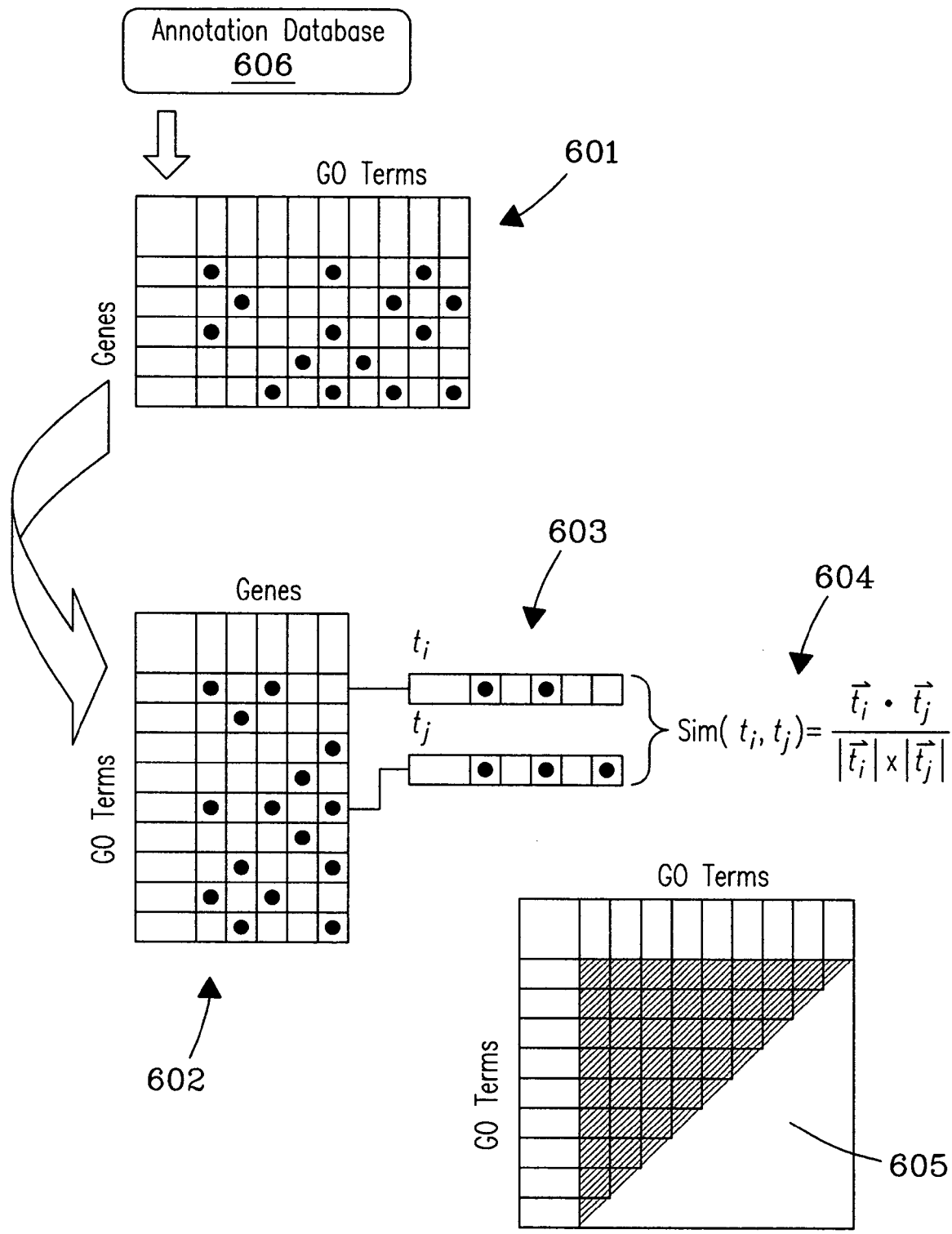
FIG. 6 is an illustration depicting an exemplary XOA calculation according to one or more embodiments of the present invention.

According to the vector space model, GO term based vector representations of genes and gene products are transformed into gene/gene product based representations of GO terms. The similarity between two vectors can then be represented by the angle between these vectors, measured by the cosine or dot product of the two, typically normalized vectors. Referring to FIG. 6, an original matrix 601 using binary values can describe the presence (e.g., "1") or absence (e.g., "0") of an association between a gene/gene product and a GO term in a given annotation database 606. The original matrix 601, expressed as genes/gene products by GO terms, is then transposed 602. In some instances, a weighting value can be applied to each binary association in order to lower the importance of an association between a GO term and a gene/gene product when a given gene/gene product is associated with many GO terms. An exemplary weighting scheme include, but is not limited to inverse document frequency (IDF). Each vector 603 can then be normalized in order to compensate for differences in the number of genes/gene products associated with GO terms. The similarity between normalized vectors can then be measured by the dot product 604, or cosine, of the two vectors, which would vary from 0 to 1. For example, a value of 0 corresponds to essentially no similarity, while a value of 1 corresponds to substantially complete similarity. GO term-GO term similarities are computed pair-wise for all GO-terms present, resulting in a cosine half-matrix 605.

For intra-scheme similarities, the information content of a GO term can depend on the number of times the term, or any child term, occurs in a database. Typically, this can be expressed as a probability consistent with embodiments described elsewhere herein and particularly in equations 2, 5, and 6. Using, for example, the vector space approach, the intra-scheme similarity measure for each pair of GO terms can be computed and stored in an information content half-matrix. The cosine half-matrix and the information content half-matrix are then used to determine XOA similarities for some or all of the possible GO-term pair combinations.

In some embodiments, textual evidence can be integrated into XOA to further enhance analysis results. Accordingly, integrating textual evidence can comprise selecting salient information from one or more sources and extracting the appropriate textual evidence. Exemplary extraction techniques can comprise information retrieval and text mining techniques and can include, but are not limited to feature weighting and selection techniques—e.g., term frequency-inverse document frequency (tf-idj) and Information Gain—as well as keyword capabilities coupled with term extraction and ontological annotation techniques. Additional techniques exist and can be encompassed by the scope of the present invention.

The output of the term extraction process can then be used to create vector-based signatures that can be compared using a similarity measure, examples of which are described elsewhere herein. The vector-based signatures can then be fused with embodiments of XOA by normalizing the vectors from the two measures and then combining them to provide an interpretable integrated model. Alternatively, a prediction model can be constructed using, for example, the XOA scores and the log-cosine (LC) as predictors without the constraint of remaining interpretable.

Example

Integrating Textual Evidence from GoPubMed Term Extraction into XOA

Details regarding the integration of textual evidence from GoPubMed term extraction into XOA are described by Sanfilippo et al. ("Integrating Ontological Knowledge and Textual Evidence in Estimating Gene and Gene Product Similarity." *Proceedings of BioNLP '06: Linking Natural Language Processing and Biology.* New York, Jun. 8, 2006.), which details are incorporated herein by reference. Details regarding the term extraction algorithm used in GoPubMed are described by Delfs et al. (Proc. of German Bioinformatics Conference, Bielefeld, Germany, 2004, LNBI Springer.), which details are incorporated herein by reference.

In the instant example, the data set was obtained as a 1% random sample of the human proteins described previously by Posse et al. (Proc. of International Workshops on Bioinformatics Research and Applications, 2006, Reading, U. K.), which is incorporated herein by reference. The data set consists of 2360 human protein pairs containing 1783 distinct human proteins. For each of the 1783 human proteins, a GoPubMed query was performed and up to 100 abstracts were retrieved. All the terms that were extracted by GoPubMed for each protein across the retrieved abstracts were collected.

The output of the GoPubMed term extraction was then utilized to create vector-based signatures for each of the 1783 proteins, where features were obtained by stemming the terms provided by GoPubMed and the value for each feature was derived as the tf-idf for the feature. The similarity between each of the 2360 protein pairs was calculated as the cosine value of the two vector-based signatures associated with the protein pair.

According to one approach, the XOA scores, as described by embodiments elsewhere herein, can be augmented according to a fusion approach in which the two similarity measures were first normalized to be commensurable and then combined to provide an interpretable integrated model. An exemplary normalization can be based on Resnik's information content measure, which can be commensurable to the log of the text based cosine (LC). Accordingly, one form of the fusion model for XOA based on Resnik's semantic similarity measure ($XOA_R$) is shown in Eqn. 7.

$$\text{Fusion(Resnik)} = XOA_R + LC \qquad \text{Eqn. 7}$$

Alternative forms of the fusion model can be derived from XOA based on either Lin ($XOA_L$) or Jiang and Corinth ($XOA_{JC}$), as shown in Eqns. 8 and 9, respectively.

$$\text{Fusion}(Lin) = XOA_L + LC \cdot \frac{Avg(XOA_L)}{Avg(XOA_R)} \qquad \text{Eqn. 8}$$

$$\text{Fusion}(Jiang\ \&\ Conrath) = XOA_{JC} + LC \cdot \frac{Avg(XOA_{JC})}{Avg(XOA_R)} \qquad \text{Eqn. 9}$$

According to an alternative approach, the XOA scores, as described by embodiments elsewhere herein, can be augmented by building a prediction model for BLAST bit scores (BBS) using the XOA and the LC as predictors without the constraint of remaining interpretable. The prediction models can be built based on the three XOA variants, $XOA_R$, $XOA_L$, and $XOA_{JC}$ and, in the instant example, were restricted to cubic polynomial regression models. More precisely, for each of the semantic similarity measures, a regression model was fit to BBS as shown in Eqn. 10, wherein the subscript x denotes either R, L, or JC, and the coefficients a-h are found by maximizing the Spearman rank order correlations between BBS and the regression model. This maximization can be automatically carried out by using a random walk optimization approach.

$$a(XOA_x) + b(XOA_x)^2 + c(XOA_x)^3 + \\ d(LC) + e(LC)^2 + f(LC)^3 + g(XOA_x \cdot LC) \qquad \text{Eqn. 10}$$

The coefficients used in the instant example for each semantic similarity measure are shown in Table 2.

TABLE 2

Exemplary coefficients of the regression model maximizeing Spearman rank correlation between BBS and the regression model using each of the three semantic similarity measures.

|   | Resnik | Lin | Jiang and Conrath |
|---|---|---|---|
| a | −10684.43 | 2.83453e−05 | 0.2025174 |
| b | 1.786986 | −31318.0 | −1.93974 |
| c | 503.3746 | 45388.66 | 0.08461453 |
| d | −3.952441 | 208.5917 | 4.939535e−06 |
| e | 0.0034074 | 1.55518e−04 | 0.0033902 |
| f | 1.4036e−05 | 9.972911e−05 | −0.000838812 |
| g | 713.769 | −1.10477e−06 | 2.461781 |

Referring to Table 3, results for both approaches are summarized, comparing Spearman rank correlations between BBS and the models from the fusion and regression approaches with Spearman rank correlations between BBS and XOA alone.

TABLE 3

Spearman rank order correlation coefficients between BBS and XOA, BBS and the fusion model, and BBS and the regression model. P-values for the differences between the augmented models and XOA alone are given in parentheses.

|  | XOA | Fusion | Regression |
|---|---|---|---|
| Resnik | 0.295 | 0.325 (>0.20) | 0.388 (0.0008) |
| Lin | 0.274 | 0.301 (>0.20) | 0.372 (0.0005) |
| Jiang and Conrath | 0.273 | 0.285 (>0.20) | 0.348 (0.008) |

Accordingly, integrating text-based evidence in the semantic similarity measurements can systematically improve the relationship between BLAST and XOA.

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

We claim:

1. A computer-implemented method of quantifying the similarity between a first node in a first electronic classification scheme and a second node in a second electronic classification scheme, the method comprising:
   finding, using processing circuitry, a third node among those in the first electronic classification scheme, wherein a first product value of the inter-scheme similarity value between the second and third nodes and the intra-scheme similarity value between the first and third nodes is a maximum;
   finding, using processing circuitry, a fourth node among those in the second electronic classification scheme, wherein a second product value of the inter-scheme similarity value between the first and fourth nodes and the intra-scheme similarity value between the second and fourth nodes is a maximum; and
   determining, using processing circuitry, the maximum between the first and second product values, wherein the maximum represents a measure of similarity between the first and second nodes.

2. The method as recited in claim 1, wherein the electronic classification schemes comprise nodes organized in a hierarchy and each node represents a concept.

3. The method as recited in claim 2, wherein one or more nodes are associated with one or more data items.

4. The method as recited in claim 1, wherein the electronic classification schemes are selected from the group consisting of ontologies, taxonomies, category trees, directed acyclic graphs, and combinations thereof.

5. The method as recited in claim 1, wherein the intra-scheme similarity value is determined according to an information theoretic approach, measures based on path length, measures based on feature similarity across nodes, or combinations thereof.

6. The method as recited in claim 5, wherein the intra-scheme similarity value is determined according to an information theoretic approach, further comprising:
   determining a least common superordinate (LCS) of intra-scheme node pairs; and
   determining an information content value for the least common superordinate,
   wherein the intra-scheme similarity value comprises the information content value.

7. The method as recited in claim 6, wherein the intra-scheme node pairs are the first and third nodes and the second and fourth nodes.

8. The method as recited in claim 7, further comprising accounting for the distance of each node from its respective LCS when determining the intra-scheme similarity value.

9. The method as recited in claim 1, wherein the inter-scheme similarity value is determined according to a statistical technique, a logic-based technique, a manual alignment technique, or combinations thereof.

10. The method as recited in claim 9, wherein the inter-scheme similarity value is determined according to a statistical technique, further comprising representing each node as a vector signature and performing cosine measures between inter-scheme node pairs, wherein the inter-scheme similarity values comprise the results of the cosine measures.

11. The method as recited in claim 10, wherein the inter-scheme node pairs are the first and fourth nodes and the second and third nodes.

12. The method as recited in claim 10, wherein the vector signatures comprise features selected from the group consisting of textual evidence, visual evidence, audio evidence, numerical evidence, and combinations thereof.

13. The method as recited in claim 10, wherein the vector signatures comprise gene ontology codes.

14. The method as recited in claim 1, wherein one or both of the first and second electronic classification schemes comprise an aspect of the Gene Ontology.

15. The method as recited in claim 1, further comprising integrating textual evidence into the quantification of similarity between nodes.

16. The method as recited in claim 15, wherein said integrating comprises extracting textual evidence from one or more information sources and creating vector-based signatures from the textual evidence.

17. The method as recited in claim 16, further comprising combining the vector-based signatures and the measure of similarity in a fusion model.

18. The method as recited in claim 16, further comprising combining a log of the text-based cosine and the measure of similarity in a prediction model.

19. An article of manufacture comprising non-transitory computer-readable media having programming to quantify the similarity between a first node in a first electronic classification scheme and a second node in a second classification scheme, said programming configured to control processing circuitry to implement processing comprising:
  finding a third node among those in the first electronic classification scheme, wherein a first product value of the inter-scheme similarity value between the second and third nodes and the intra-scheme similarity value between the first and third nodes is a maximum;
  finding a fourth node among those in the second electronic classification scheme, wherein a second product value of the inter-scheme similarity value between the first and fourth nodes and the intra-scheme similarity value between the second and fourth nodes is a maximum; and
  determining the maximum between the first and second product values, wherein the maximum represents a measure of similarity between the first and second nodes.

20. An apparatus comprising processing circuitry to perform processing for quantification of the similarity between a first node in a first electronic classification scheme and a second node in a second electronic classification scheme, said processing comprising:
  finding a third node among those in the first electronic classification scheme, wherein a first product value of the inter-scheme similarity value between the second and third nodes and the intra-scheme similarity value between the first and third nodes is a maximum;
  finding a fourth node among those in the second electronic classification scheme, wherein a second product value of the inter-scheme similarity value between the first and fourth nodes and the intra-scheme similarity value between the second and fourth nodes is a maximum; and
  determining the maximum between the first and second product values, wherein the maximum represents a measure of similarity between the first and second nodes.

21. The apparatus as recited in claim 20, wherein the processing circuitry is further configured to integrate textual evidence when quantifying the similarity between nodes.

* * * * *

UNITED STATES PATENT AND TRADEMARK OFFICE
CERTIFICATE OF CORRECTION

PATENT NO. : 7,805,010 B2
APPLICATION NO. : 11/493503
DATED : September 28, 2010
INVENTOR(S) : Christian Posse et al.

It is certified that error appears in the above-identified patent and that said Letters Patent is hereby corrected as shown below:

col. 3, lines 38 through 44 should be deleted as they are duplicative;

col. 9, table 1, first column, row 49: GO:0008264 (BP) --- should be replaced to read: GO:0008284 (BP); and col. 13, line 52: (tf-idj) --- should be replaced to read: (tf-idf).

Signed and Sealed this
Twenty-second Day of February, 2011

David J. Kappos
*Director of the United States Patent and Trademark Office*